(12) United States Patent
Zheng et al.

(10) Patent No.: US 10,920,183 B2
(45) Date of Patent: Feb. 16, 2021

(54) PETRI DISH

(71) Applicant: Thermo Fisher Scientific (Shanghai) Instrument Co., Ltd., Shanghai (CN)

(72) Inventors: Guo Min Zheng, Shanghai (CN); Bo Li, Suzhou (CN)

(73) Assignee: Thermo Fisher Scientific (Shanghai) Instrument Co., Ltd., Shanghai (CN)

(*) Notice: Subject to any disclaimer, the term of this patent is extended or adjusted under 35 U.S.C. 154(b) by 720 days.

(21) Appl. No.: 15/038,908

(22) PCT Filed: Nov. 11, 2015

(86) PCT No.: PCT/CN2015/094267
§ 371 (c)(1),
(2) Date: May 24, 2016

(87) PCT Pub. No.: WO2016/074614
PCT Pub. Date: May 19, 2016

(65) Prior Publication Data
US 2017/0166851 A1    Jun. 15, 2017

(30) Foreign Application Priority Data

Nov. 11, 2014 (CN) .......................... 20142066829.6
Nov. 21, 2014 (CN) ......................... 201420703664.X

(51) Int. Cl.
*C12M 1/22* (2006.01)
*C12M 1/00* (2006.01)

(52) U.S. Cl.
CPC .............. *C12M 23/10* (2013.01); *C12M 1/22* (2013.01); *C12M 23/38* (2013.01)

(58) Field of Classification Search
CPC .......... C12M 1/22; C12M 23/10; C12M 23/38
(Continued)

(56) References Cited

U.S. PATENT DOCUMENTS

| 3,649,463 A | 3/1972 | Buterbaugh |
| 4,160,700 A | 7/1979 | Boomus et al. |

(Continued)

FOREIGN PATENT DOCUMENTS

| CN | 202543203 U | 11/2012 |
| CN | 102943036 A | 2/2013 |

(Continued)

OTHER PUBLICATIONS

Dongfang Zhu, "English machine translation of Chinese document CN 202543203U". (Year: 2012).*

(Continued)

*Primary Examiner* — Liban M Hassan
(74) *Attorney, Agent, or Firm* — Wood Herron & Evans LLP

(57) ABSTRACT

The present invention relates to a Petri dish comprising a dish body which comprises a bottom wall and a side wall which extends along an outer circumference of the bottom wall, the bottom wall and the side wall of the dish body form an upper opening space adapted to accommodate cultures; a dish lid adapted to cover the upper opening space from above the dish body, the dish lid comprises a top wall and a side wall which extends along an outer circumference of the top wall, wherein the dish body and the dish lid are two independent members that are detachable, and the side wall of the dish body is formed on the outer side thereof with a ring for gripping that extends circumferentially, and the ring for gripping having an outer diameter larger than that of the dish lid. The Petri dish according to the present invention has a simple structure. Through the ring for gripping on the dish body, the user can easily hold the dish body without accidentally dislodging the dish lid or sliding it off the dish body.

20 Claims, 6 Drawing Sheets

(58) Field of Classification Search
USPC ....................................................... 435/305.4
See application file for complete search history.

(56) References Cited

U.S. PATENT DOCUMENTS

| | | | |
|---|---|---|---|
| 5,856,176 | A | 1/1999 | Mathus et al. |
| 2011/0003376 | A1 | 1/2011 | Gulzow et al. |

FOREIGN PATENT DOCUMENTS

| | | |
|---|---|---|
| CN | 102943038 A | 2/2013 |
| CN | 202849413 U | 4/2013 |
| CN | 202989149 U | 6/2013 |
| CN | 103555578 A | 2/2014 |
| CN | 204369882 U | 6/2015 |
| CN | 204455118 U | 7/2015 |
| EP | 119984 A1 | 9/1984 |
| WO | 97036992 A1 | 10/1997 |
| WO | 2010128569 A1 | 11/2010 |
| WO | 2011055560 A1 | 5/2011 |
| WO | 2013158666 A1 | 10/2013 |

OTHER PUBLICATIONS

ESPACENET, English Machine Translation of Abstract for EP0119984A1, published Sep. 26, 1984, retrieved from http://worldwide.espacenet.com on May 13, 2016 (2 pages).
ESPACENET, English Machine Translation of Abstract for CN202543203U, published Nov. 21, 2012, retrieved from http://worldwide.espacenet.com on May 13, 2016 (1 page).
ESPACENET, English Machine Translation of Abstract for CN102943036A, published Feb. 27, 2013, retrieved from http://worldwide.espacenet.com on May 16, 2016 (1 page).
ESPACENET, English Machine Translation of Abstract for CN102943038A, published Feb. 27, 2013, retrieved from http://worldwide.espacenet.com on May 16, 2016 (1 page).
ESPACENET, English Machine Translation of Abstract for CN202849413U, published Apr. 3, 2013, retrieved from http://worldwide.espacenet.com on May 16, 2016 (1 page).
ESPACENET, English Machine Translation of Abstract for CN202989149U, published Jun. 12, 2013, retrieved from http://worldwide.espacenet.com on May 16, 2016 (1 page).
ESPACENET, English Machine Translation of Abstract for CN103555578A, published Feb. 5, 2014, retrieved from http://worldwide.espacenet.com on May 13, 2016 (1 page).
ESPACENET, English Machine Translation of Abstract for CN204369882U, published Jun. 3, 2015, retrieved from http://worldwide.espacenet.com on May 13, 2016 (1 page).
ESPACENET, English Machine Translation of Abstract for CN204455118U, published Jul. 8, 2015, retrieved from http://worldwide.espacenet.com on May 13, 2016 (1 page).
State Intellectual Property Office of the P.R. China, International Search Report and Written Opinion of the International Searching Authority, International Application No. PCT/CN2015/094267, dated Feb. 14, 2016 (14 pages).
Anonymous: "Petri Dishes", Isolab Laborgerate GmbH, Catalogue 2015, p. 189, Lab Consumables & Labware, XP002782523, retrieved from Internet URL:http://www.isolab.de/Assets/upload/editor/isolab_2015_catalog_189.pdf (1 page).
European Patent Office, Supplementary European Search Report, Application No. 15859089.3, dated Jul. 13, 2018 (12 pages).
Patent Office of the People's Republic of China, Office Action, Chinese Application No. 201580072756.X, dated Dec. 3, 2019 (8 pages).

* cited by examiner

PETRI DISH

CROSS-REFERENCE TO RELATED APPLICATIONS

This application is a submission under 35 U.S.C. § 371 of International Application No. PCT/CN2015/094267, filed Nov. 11, 2015, which claims priority to Chinese Application Nos. 201420668293.6, filed Nov. 11, 2014 and 201420703664.X, filed Nov. 21, 2014, the disclosures of which are hereby expressly incorporated by reference herein in their entireties.

FIELD OF THE INVENTION

The present invention relates to eukaryotic cell or prokaryotic cell (microbe) culturing and, more particularly, to a Petri dish for facilitating operation.

BACKGROUND OF THE INVENTION

As a dish for culture medium, the Petri dish has been used for decades in the technical field of cell or microbe culturing, and is frequently used in the lab. The Petri dish generally has a circular shape, and consists of a dish body for accommodating the culture medium and a dish lid which matches with the dish body. The dish lid is placed onto the dish body so as to prevent the culture medium from being contaminated by microbes or the like from an external environment. Meanwhile, the dish lid allows air to pass through so as to facilitate survival, growth, observation and detection of cells or microbes. The material for manufacturing the Petri dish comprises glass, synthetic resin, silica and corrosion-resistant metal (rarely used), etc.

FIGS. 1 and 2 show the structures of two commonly used Petri dishes in the prior art.

The structure of the Petri dish shown in FIG. 1 is very simple, wherein both the dish body 1 and the dish lid 2 have a regular circular shape. When operating the Petri dish, a user typically places the Petri dish onto a bio-safety cabinet or a cabinet plate of a dust free cabinet. When performing an operation on the Petri dish, the user can use his/her left hand (for a right-handed person) to half open the dish lid 2, and use the right hand to hold a liquid transfer pipettor so as to perform such operations as liquid transfer, liquid intake or liquid refill, etc. Since the dish body 1 is on the left hand of the user, the left hand cannot cooperatively engage in an accurate operation when the right hand holds the liquid transfer pipettor to operate. Meanwhile, it is inappropriate for an opening of the dish lid 2 to be overly large when the dish lid 2 is opened/closed since an external contaminant may enter the inside of the Petri dish. Once the operation is completed, the dish lid 2 has to be closed immediately so as to avoid contamination. This necessitates that the operator has a highly developed skill level and be very cautious. Moreover, when the user moves the Petri dish, it is required to hold the dish body or grip the outer ring of the Petri dish with hand; often, the user may carelessly grasp the dish lid, thinking that he has grasped the whole Petri dish. At best, the dish lid will be opened to a great extent, causing internal contamination; and at worst, the dish body will be lifted up together with the dish lid, and may fall off during moving.

As compared to the Petri dish shown in FIG. 1, the Petri dish shown in FIG. 2 additionally has a ring for gripping 3 on the dish body, and the round of ring for gripping 3 has an outer diameter that is the same as the maximum outer diameter of the dish lid 2 so that the user can stably hold the Petri dish when moving the Petri dish. However, if the user is careless, he may only take hold of the dish lid by accident without catching the ring for gripping, thus leading to a consequence that is the same as that in the Petri dish shown in FIG. 1. At best, the dish lid will be opened to a great extent, causing internal contamination; and at worst, the dish body will be lifted up together with the dish lid, and may fall off during moving. The lid opening operations in liquid transfer, liquid intake or liquid refill are consistent with the method of operating the Petri dish described in connection with the structure shown in FIG. 1

Moreover, for the Petri dishes shown in FIGS. 1 and 2, when the user grips the dish body and opens the dish lid, there are also some inconveniences. An experienced operator will use the left hand to hold the Petri dish, wherein the little finger, the ring finger and the middle finger are used to hold the dish body 1, and the thumb and index finger are used to open the dish lid 2. However, such an operation is unstable since only three fingers are used to hold the dish body. Besides, such an operation requires that the user has certain practice and has gained certain experience, and is not applicable to a small-sized Petri dish. Once the Petri dish slides off, the cultures in the Petri dish will be contaminated. Moreover, since the material of the Petri dish is fragile, the Petri dish may be damaged if it falls off from a large height. These accidents will influence the progress and result of biotic experiments.

SUMMARY OF THE INVENTION

The technical problem to be solved by the present invention is to provide a Petri dish that can be easily hand-held and can be operated single-handedly.

In order to address the above described technical problem, the present invention provides a Petri dish which comprises:

a dish body which comprises a bottom wall and a side wall which extends along an outer circumference of the bottom wall, the bottom wall and the side wall of the dish body form an upper opening space adapted to accommodate cultures;

a dish lid adapted to cover the upper opening space from above the dish body, the dish lid comprises a top wall and a side wall which extends along an outer circumference of the top wall; and the dish body and the dish lid are two independent members that are detachable, and the side wall of the dish body is formed on the outer side thereof with a ring for gripping that extends circumferentially, and the ring for gripping having an outer diameter larger than that of the dish lid.

Optionally, in the above-described Petri dish, a plurality of upwardly extending protrusions is distributed on the ring for gripping.

Optionally, in the above-described Petri dish, a top face of the protrusions is formed into an upwardly opening hook shape, and when the dish cover is closed on the dish body, a lower end of the side wall of the dish lid is located in the opening.

Optionally, in the above-described Petri dish, the protrusions are evenly distributed on the ring for gripping in a circumferential direction.

Optionally, in the above-described Petri dish, the Petri dish has a circular shape and an extension length between two protrusions along the circumferential direction of the side wall of the dish body corresponds to a central angle of 20 degrees to 80 degrees, and preferably corresponds to a central angle of 50 degrees.

Optionally, in the above-described Petri dish, the ring for gripping has an upwardly angled brim portion on a radially outer circumference side, and when the dish lid is closed on the dish body, the upwardly angled brim portion surrounds a lower end of the side wall of the dish lid.

Optionally, in the above-described Petri dish, the ring for gripping comprises ring sections for gripping spaced-apart by gaps, and the upwardly angled brim portion is located on the ring sections for gripping.

Optionally, in the above-described Petri dish, only an end portion of the ring sections for gripping is provided with the upwardly angled brim portion.

Optionally, in the above-described Petri dish, the ring sections for gripping are symmetrically or evenly distributed in a circumferential direction on the side wall of the dish body.

Optionally, in the above-described Petri dish, the Petri dish has a circular shape and the length by which the gaps extend in a circumferential direction of the side wall of the dish body corresponds to a central angle of 20 degrees to 80 degrees, and preferably corresponds to a central angle of 50 degrees.

Optionally, in the above-described Petri dish, the maximum opening angle α of the dish lid relative to the dish body is between 20 degrees and 70 degrees, and is preferably 45 degrees.

Optionally, in the above-described Petri dish, the length by which a side wall lower portion of the dish lid extends in an axial direction of the dish lid is slightly larger than the length by which the portion of a side wall upper portion of the dish body that is above the ring for gripping extends in an axial direction of the dish body.

Optionally, in the above-described Petri dish, the side wall of the dish lid is partially formed to be an outwardly angled brim portion, and the dish lid can be opened by pressing the outwardly angled brim portion towards the side wall of the dish body.

Optionally, in the above-described Petri dish, the number of the outwardly angled brim portion is more than one and the outwardly angled brim portions are distributed symmetrically or evenly along the circumference of the dish lid.

Optionally, in the above-described Petri dish, the Petri dish is a circular Petri dish, and the curvature of the outwardly angled brim portion is consistent with the curvature of the side wall of the dish body.

Optionally, in the above-described Petri dish, the ring for gripping is continuous or spaced apart by gaps, and the ring for gripping does not interfere with the side wall of the dish lid.

Optionally, in the above-described Petri dish, when the outwardly angled brim portion abuts the side wall of the dish body, the opening angle of the dish lid relative to the dish body is between 20 degrees and 70 degrees, and is preferably 45 degrees.

Optionally, in the above-described Petri dish, the Petri dish has a circular shape and the length by which the outwardly angled brim portion extends along the circumferential direction of the side wall of the dish lid corresponds to a central angle of 20 degrees to 80 degrees, and preferably corresponds to a central angle of 50 degrees.

Optionally, in the above-described Petri dish, a top portion of the dish lid defines a receiving space slightly larger than a bottom portion of the dish body.

Optionally, in the above-described Petri dish, the bottom of the dish body defines an air circulating space.

Optionally, in the above-described Petri dish, a plurality of spaced-apart protrusions are evenly distributed circumferentially at a portion where a bottom face of the top wall of the dish lid is joined to an inner side of the side wall of the dish lid.

Optionally, in the above-described Petri dish, the Petri dish has a non-circular shape, e.g., rectangular, square, trapezoidal, triangular or oval.

It can be understood that the Petri dish according to the present invention has a simple structure. Through the ring for gripping on the dish body, the user can easily hold the dish body without accidentally dislodging the dish lid or sliding the lid off the dish body. Moreover, the arrangement of the protrusions on the ring for gripping as well as the upwardly angled brim portion on the ring sections for gripping also realizes a single-handed operation on the dish lid, thus enabling a more accurate operation such as liquid transfer, liquid intake or liquid refill, etc.

BRIEF DESCRIPTION OF THE DRAWINGS

The disclosure of the present invention will become more apparent with reference to the accompanying drawings. It should be understood that these drawings are merely provided for the purpose of illustration, and are not intended to limit the scope of protection of the present invention, wherein.

DETAILED DESCRIPTION OF THE INVENTION

The specific embodiments of the present invention will be described in detail below with reference to the accompanying drawings. The terms "upper", "lower", "inner" and "outer" or the like for indicating orientation referred to herein are defined with reference to the orientation of the Petri dish when the Petri dish is in normal use in the art. It should be understood that the orientation terms used herein should not be taken as limiting the scope of protection of the present invention.

First Embodiment

Figure 1:
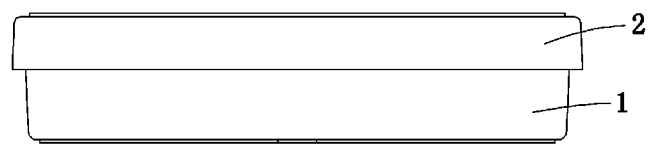
FIGS. 1 and 2 are schematic side views of Petri dishes in the prior art.
Figure 2:
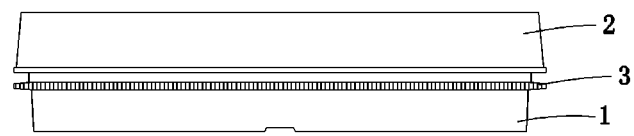
Figure 3:
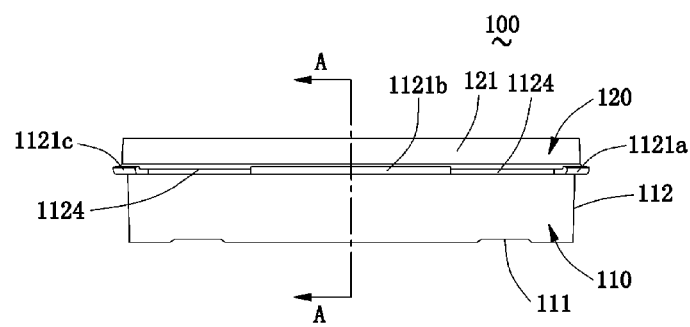
FIG. 3 is a schematic side view of a Petri dish according to a first embodiment of the present invention.

FIG. 3 is a schematic side view of a Petri dish according to the first embodiment of the present invention. In FIG. 3, reference sign 100 generally indicates a Petri dish, 110 indicates a dish body, 111 indicates a bottom wall of the dish body, 112 indicates a side wall of the dish body, 1121 (including 1121a, 1121b, 1121c, etc.) indicates the rings for gripping on the side wall of the dish body, 1124 indicates gaps in the rings for gripping, 120 indicates a dish lid, and 121 indicates a side wall of the dish lid.

Optionally, the Petri dish 100 can be a circular Petri dish. As can be seen in the figure, the Petri dish 100 comprises a dish body 110 and dish lid 120 that can be separated from each other, wherein the dish body 110 comprises a bottom wall 111 and a side wall 112, the dish lid 120 comprises a side wall 121 and a top wall 122 (see FIG. 4), and the dish lid 120 can be placed onto the dish body 110 to cover it. Rings for gripping 1121 are formed at the outside of the side wall 112 of the dish body 110 and have an outer diameter larger than that of the dish lid. The rings for gripping 1121 enable the user to easily grip the dish body 110 without accidentally holding the dish lid 120 and dislodging the dish lid or sliding it off the dish body. The rings for gripping can either extend continuously along the entire circumference or be spaced-apart by several gaps. In this embodiment, the rings for gripping 1121 are arranged to be of the spaced-apart type and comprise several ring sections for gripping that are spaced-apart by gaps 1124, such as a first ring section for gripping 1121a, a second ring section for gripping 1121b, and a third ring section for gripping 1121c, etc. Preferably but not necessarily, the outer periphery of the rings for gripping 1121 may be serrated for facilitating a more stable grip.

According to the illustrated embodiment of the present invention, upwardly angled brim portions are provided on the circumferential outer side of the rings for gripping 1121. Specifically, the upwardly angled brim portions are provided on the circumferential outer side of the first ring section for gripping 1121a, a second ring section for gripping 1121b, and a third ring section for gripping 1121c, etc. When the dish lid 120 is closed, a lower end of the side wall 121 of the dish lid is received in the upwardly angled brim portions of the rings for gripping and is surrounded by the upwardly angled brim portions. Such an arrangement brings about the following advantage: the largest outer edge of the Petri dish is an outer ring of the upwardly angled brim portions of the rings for gripping, rather than the original outer ring of the dish lid; therefore, when the user grips the Petri dish, he can directly take hold of the upwardly angled brim portions of the rings for gripping to perform a safe and stable movement. In this way, the dish lid will not be touched during the movement, thus avoiding an accident where the dish lid is dislodged or the dish body falls off during movement. Since no gap 1124 exists in an embodiment in which the rings for gripping 1121 extend continuously along the entire circumference on the side wall of the dish body 110, when the dish lid is closed, the upwardly angled brim portions of the rings for gripping can partially or wholly surround the lower end of the side wall of the dish lid.

As described above, the rings for gripping 1121 having upwardly angled brim portions in FIG. 3 do not completely extend along the entire circumference of the side wall of the dish body. Four gaps 1124 are evenly disposed in FIG. 3, wherein the four gaps are of the same size. Gaps having a different number and/or different sizes are also possible as actually required in optional embodiments. The gaps for rings for gripping enable the user to grip the dish lid conveniently and directly with his fingers. In some cases, the user has to open the dish lid completely. If so, the user can grip the dish lid directly with his fingers from the gaps. Meanwhile, such a design of gaps can also assist in a single-handed operation of opening the dish lid in which the users uses two ends of the gaps as support points and uses the thumb to press a side edge of a top portion of the dish lid. In this way, the dish lid 120 can pivot and open about the end portions of the ring sections of gripping at the ends of a gap 1124. It can be understood that the sizes of the gaps 1124 will influence the maximum opening angle α (see FIG. 5) of the dish lid 120 and the stability in opening the dish lid. When the gaps are overly large, a lower edge of the side wall of the dish lid will be prone to abut the side wall of the dish body, which will influence the opening angle; and when gaps are overly small, the stability in opening the dish lid will be impaired, and the dish lid will be prone to incline towards two sides or even fall off towards two sides. Such a design is also applicable to a single-handled operation of a small-sized Petri dish.

Figure 4:
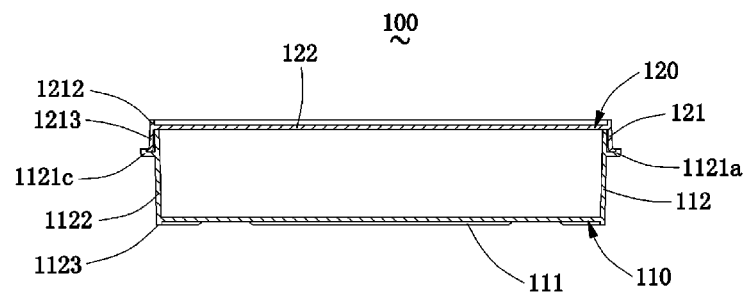
FIG. 4 is a schematic sectional view taken along the line A-A in FIG. 3, wherein the Petri dish is shown in a closed state.

FIG. 4 is a schematic sectional view taken along the line A-A in FIG. 3, wherein the Petri dish is shown in a closed state. In FIG. 4, the reference sign 122 indicates the top wall of the dish lid 120.

For the purpose of facilitating description, the portion of the side wall 121 of the dish lid 120 that is above the top wall 122 is referred to as side wall upper portion 1212, and the portion of the side wall 121 of the dish lid 120 that is below the top wall 122 is referred to as side wall lower portion 1213. As shown, the side wall upper portion 1212 and the side wall lower portion 1213 can respectively define an upper receiving space and a lower receiving space that are above and below the top wall 122 of the dish lid 120 respectively. Generally, the length by which the side wall upper portion 1212 extends in an axial direction of the dish lid is shorter than the length by which the side wall lower portion 1213 extends in an axial direction of the dish lid. That is, the upper receiving space is shallower than the lower receiving space. The diameter of the upper receiving space defined by the side wall upper portion 1212 is slightly larger than an outer diameter of an end portion at a lower end of the dish body 110. That is, the area of the upper receiving space formed by the upper portion of the side wall of the dish lid is slightly larger than the area of the lower end of the dish body. The diameter of the lower receiving space defined by the side wall lower portion 1213 is slightly larger than an outer diameter of an end portion at an upper end of the dish body 110. That is, the area of the lower receiving space formed by the lower portion of the side wall of the dish lid is slightly larger than the area of the upper end of the dish body. It can be understood that such a design enables two identical Petri dishes to be stacked on each other by simply placing one Petri dish into the upper receiving space at the top of the other Petri dish. Moreover, the dish cover 120 can easily cover the dish body 110. In a preferred but non-necessary embodiment, in order to facilitate the opening and closing of the dish lid 120 on the dish body 110, the side wall lower portion 1213 of the dish lid as well as the lower receiving space defined by the side wall lower portion 1213 can be designed to have a truncated cone shape, wherein the inner diameter at the lower end is slightly larger than the inner diameter at the position where it is joined to the top wall 122 of the dish lid 120. However, for the present invention, these features are also optional, not indispensable. For example, in some specific embodiments, it is also possible that the dish lid is not provided with the above described receiving spaces.

For the purpose of facilitating description, the portion of the side wall 112 of the dish body 110 that is above the bottom wall 111 is referred to as side wall upper portion 1122, and the portion of the side wall 112 of the dish body 110 that is below the bottom wall 111 is referred to as side wall lower portion 1123. The side wall upper portion 1122 and the side wall lower portion 1123 respectively define an upper opening space and a lower opening space that are above and below the bottom wall 111 of the dish body 110 respectively. The upper opening space defined by the side wall upper portion 1122 is used for receiving cultures, and the lower opening space defined by the side wall lower portion 1123 is an air circulating space for avoiding a contact between the bottom wall 111 of the dish body 110 and other objects under the Petri dish, thus keeping the bottom wall 111 from an influence exerted by uneven temperatures. Meanwhile, such a design in structure can also increase the structural strength at the bottom of the dish body. In a preferred but non-necessary embodiment, the side wall lower portion 1123 of the dish body 110 can have one or more gaps that are distributed circumferentially so that an air circulation can be realized between the lower opening space and the outside, thus achieving a temperature equilibrium at the bottom wall 111 of the dish body 110. As shown, the side wall 112 of the dish body 110 can be also designed to have a truncated cone shape, wherein the outer diameter at the lower end is slightly smaller than the inner diameter of the upper receiving space defined by the side wall upper portion 1212 of the dish lid 120. As shown, optionally in this embodiment, the side wall upper portion 1122 of the dish body 110 as well as the upper opening space defined by the side wall upper portion 1122 can be designed to have a truncated cone shape, and the outer diameter at the side wall lower portion 1123 is slightly smaller than the inner diameter of the upper receiving space defined by the side wall upper portion 1212 of the dish lid 120. The design of the truncated cone shape of the side wall portions of the dish body 110 and the dish lid 120 can also facilitate a pulling out operation after molding. It can be understood that for the present invention, the truncated cone shape of the lower opening space and the side walls of the dish body and the dish lid is also optional, not indispensable. For example, in some specific embodiments, it is also possible that the Petri dish is not provided with these features.

It can be understood that in an alternative embodiment, the inner diameter of the side wall lower portion 1213 of the dish lid 120 at the position where it is joined to the top wall 122 is slightly larger than the outer diameter at the top end of the side wall upper portion 1122 of the dish body 110. A plurality of spaced-apart protrusions can be evenly distributed in a circumferential direction at a position where the bottom surface of the top wall 122 of the dish lid 120 is joined to the inner side of the side wall lower portion 1213. At this time, the length by which the side wall lower portion 1213 of the dish lid 120 extends in an axial direction of the dish lid can be slightly smaller than the length by which the portion of the side wall upper portion 1122 of the dish body 110 that is above the rings for gripping 1121 extends in an axial direction of the dish body. These protrusions enables a clearance to be formed between the bottom face of the top wall 122 of the dish lid 120 and the top portion of the side wall 112 of the dish body 110 so that air can pass through. Or alternatively, the length by which the side wall lower portion 1213 of the dish lid 120 extends in an axial direction of the dish lid can be slightly larger than the length by which the portion of the side wall upper portion 1122 of the dish body 110 that is above the rings for gripping 1121 extends in an axial direction of the dish body so that when the dish lid 120 is placed onto the dish body, an air circulating clearance is formed between the top wall 122 of the dish lid 120 and the side wall upper portion 1122 of the dish body, and an air circulating path to the outside is formed at the gaps of the rings for gripping. In such a situation, if the rings for gripping 1121 are provided with gaps 1124, the above described protrusion may not be additionally disposed.

Figure 5:
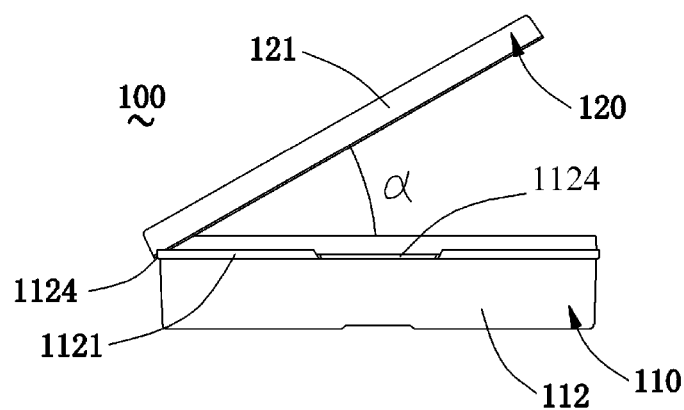
FIG. 5 is another schematic side view of the Petri dish according to the above first embodiment of the present invention, wherein the Petri dish is shown in an open state.

FIG. 5 is another schematic side view of the Petri dish according to the above first embodiment of the present invention, wherein the Petri dish is shown in an open state. As shown, in case where the user uses his hand (not shown) to perform an operation, the dish lid 120 is pivoted to be opened in a state where two ends of the left gap 1124 of the rings for gripping are used as pivoting points, and the opening state of the dish lid 120 is maintained in a state where the two ends are used as supporting points, thus making both the single-handed operation and maintenance very convenient. The "a" in FIG. 5 is a maximum opening angle of the dish lid 120 relative to the dish body 110. Such an angle is generally reached when the dish lid 120 is pivoted about the two ends of the left gap 1124 shown in the figure until a lowest portion of the lower edge of the side wall 121 of the inclined dish lid abuts an outer side of the side wall 112 of the dish body. The range of this angle α is between 20 degrees and 70 degrees, and is preferably 45 degrees. An opening angle that is overly large or small may cause an unstable fit between the opened dish lid and the dish body, or hamper an operation such as liquid transfer, liquid intake or liquid refill, etc.

Figure 6:
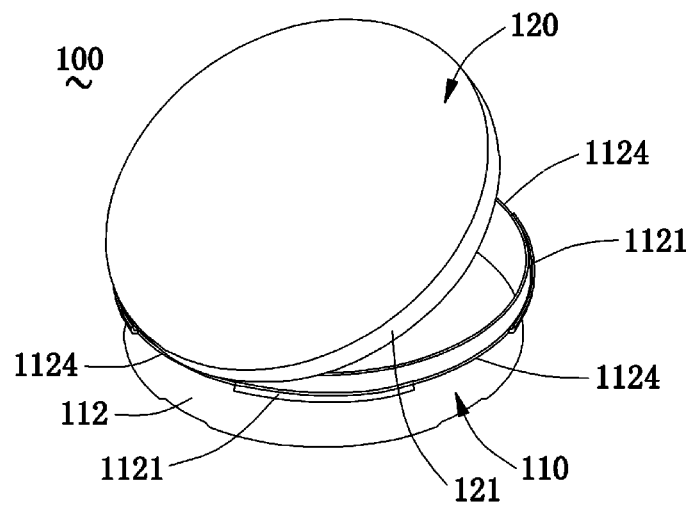
FIG. 6 is a perspective view of the Petri dish according to the above first embodiment of the present invention, wherein the Petri dish is shown in an open state.

FIG. 6 is a perspective view of the Petri dish according to the above first embodiment of the present invention, wherein the Petri dish is shown in an open state. It can be understood that the size of the gaps 1124 of the rings for gripping, i.e., the extending length along the circumference of the side wall of the dish body should not be overly large or overly small. Otherwise, as described above with reference to FIG. 3, the opening will be overly small when the dish lid is opened or the dish lid will not be held stably beside the dish body. Ideally, the length by which the gaps extend along the circumferential direction of the side wall of the dish body corresponds to a central angle of 20 degrees to 80 degrees, and preferably corresponds to a central angle of 50 degrees.

It can be understood that the Petri dish in FIGS. 5 and 6 can be also opened at other gaps in the same manner.

Second Embodiment

Figure 7:
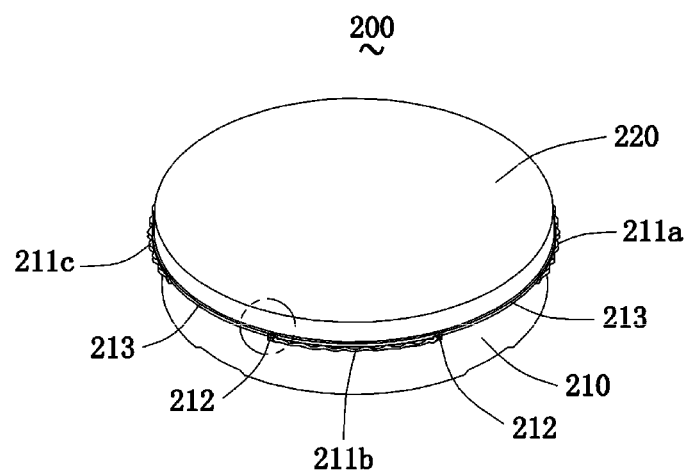
FIG. 7 is a perspective view of a Petri dish according to a second embodiment of the present invention, wherein the Petri dish is shown in a closed state.
Figure 8:
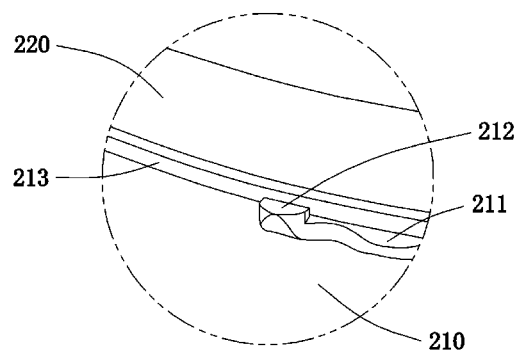
FIG. 8 is a partial enlarged schematic view of the circled portion in FIG. 7.

FIG. 7 is a perspective view of a Petri dish according to the second embodiment of the present invention, wherein the Petri dish is shown in a closed state. The Petri dish 200 according to this embodiment comprises a dish body 210 and a dish lid 220. The side wall of the dish body of the Petri dish 200 is provided with a noncontinuous ring for gripping 211 having an outer diameter larger than that of the dish lid 220 (at least at the lower end of the side wall). The ring for gripping 211 comprises several ring sections for gripping 211a, 211b, 211c, etc., that are spaced-apart by gaps 213. Upwardly angled brim portions 212 are only formed at two ends of each ring section for gripping and are used as pivoting points when the dish lid is being opened and as supporting points after the dish lid is opened. The upwardly angled brim portions disposed at each end of the ring section for gripping 211b are identified in detail in the figure. It can be understood that the upwardly angled brim portions can be also disposed at two ends of other ring sections for gripping 211a and 211c. In the alternative embodiment shown in the figure, in order to ensure the stability in grip, the outer circumferential surface of each portion of the ring section for gripping 211 is also formed with a serrated structure. FIG. 8 is a partial enlarged schematic view of the circled portion in FIG. 7, wherein the structure of the upwardly angled brim portions 212 can be seen clearly. It can be understood that the above description of the dish body and the dish lid with reference to FIGS. 3-6 as well as various variations of the embodiments will also apply to the embodiment shown in FIGS. 7 and 8, and are not discussed repeatedly.

Third Embodiment

Figure 9:
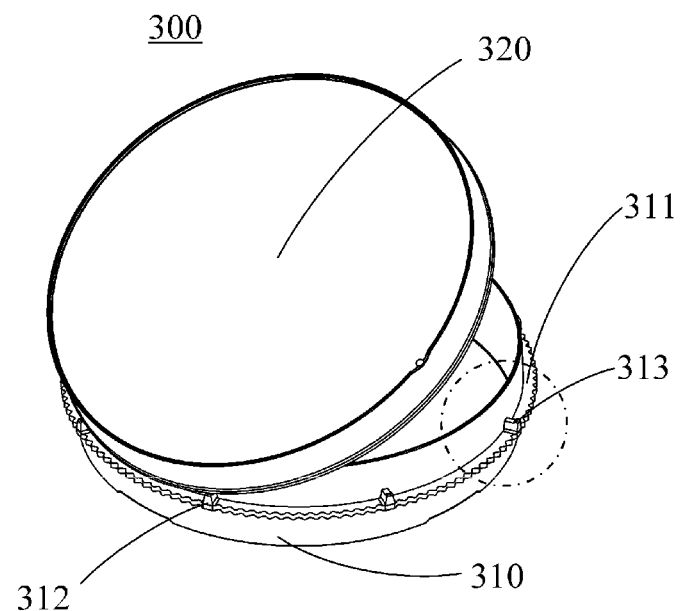
FIG. 9 is a perspective view of a Petri dish according to a third embodiment of the present invention, wherein the Petri dish is shown in an open state.
Figure 10:
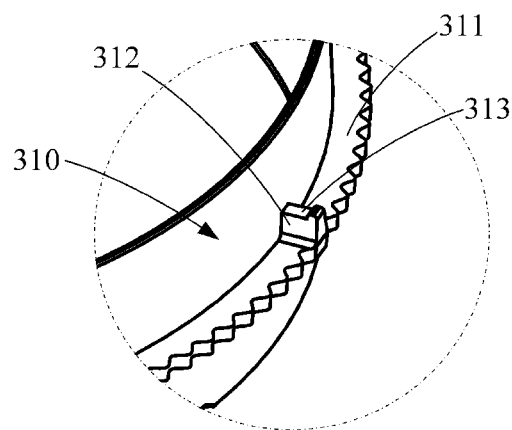
FIG. 10 is partial enlarged schematic view of the circled portion in FIG. 9.

FIG. 9 is a perspective view of a Petri dish according to the third embodiment of the present invention, wherein the Petri dish is shown in an open state. Reference sign 300 in FIG. 9 generally indicates a Petri dish, 310 indicates a dish body, 311 indicates a ring for gripping, 312 indicates protrusions, 313 indicates a hook structure opening upwardly, and 320 indicates a dish lid. As shown, the dish lid and the dish body are two independent members that can be separated. The ring for gripping 311 extends circumferentially on the side wall of the dish body 310 and extends over the entire circumference of the side wall of the dish body 310. In an alternative embodiment, the outer diameter of the ring for gripping 311 can be larger than that of the dish lid 320, and the outer circumference side of the ring for gripping 311 can be also formed with serrations. Several protrusions 312 that extend upwardly are distributed on the ring for gripping 311 and the protrusions 312 are preferably distributed evenly in the circumferential direction. It can be also seen from the figure that a hook structure 313 opening upwardly is formed on a top face of each protrusion 312. It can be understood that when the dish lid 320 covers and closes on the dish body 310, a lower end of the side wall of the dish lid 320 will fall into an opening of the hook structure 313. When a proper position on the upper edge of the dish lid 320 is pressed, the dish lid 320 will pivot about a corresponding protrusion 312 or hook structure 313 (if the protrusion 312 is formed with the hook structure 313) so that the dish lid 320 is opened. In this embodiment, the extending length between two protrusions in the circumferential direction of the side wall of the dish body can also correspond to a length of the gaps 1124, 213 described above with reference to the first, the second embodiments, i.e., corresponds to a central angle of 20 degrees to 80 degrees, and preferably corresponds to a central angle of 50 degrees. The pivoting opening angle of the dish lid 310 can be also set to have the same characteristics as the maximum opening angle α in the above embodiment. FIG. 10 is partial enlarged schematic view of the circled portion in FIG. 9, wherein the structures of the protrusion 312 and the hook structure 313 can be clearly seen. Moreover, the above description of the dish body and the dish lid with reference to FIGS. 3-6 as well as various variations of the first embodiments will also apply to the third embodiment shown in FIGS. 9 and 10, and are not discussed repeatedly.

Figure 11A:
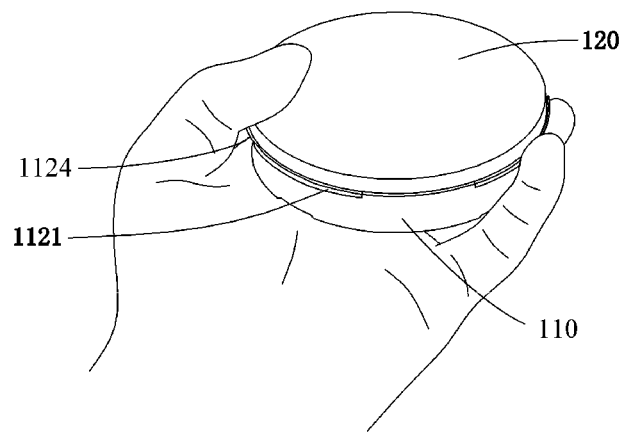
FIGS. 11a and 11b schematically show how the Petri dish according to the first embodiment of the present invention is operated.
Figure 11B:
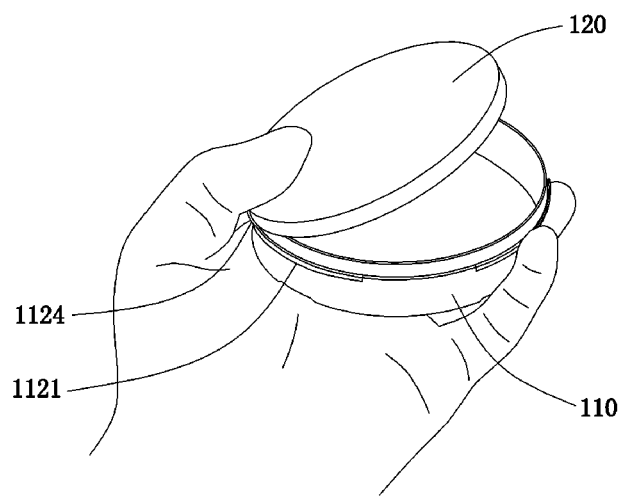

FIGS. 11a and 11b schematically show how the Petri dish according to one embodiment of the present invention is operated. When a user opens the Petri dish, the Petri dish can be hand-held as shown in FIG. 11a so that the whole Petri dish is in the palm and the position of the thumb right aims at a position on the dish lid 120 which aligns with a certain gap 1124 on the ring for gripping 1121 of the dish body 110. If the thumb does not aim at the position properly, the thumb can turn the dish lid around so that the thumb can aim at the position. When the user needs to open the Petri dish to perform an operation, he only has to press an upper edge of the dish lid with his thumb so that the dish lid will pivot about two ends of the gap 1124 and will be opened. At this time, the whole Petri dish is still steadily held in the palm, and the left hand can cooperate with the right hand (which grips an appliance such as the liquid transfer pipettor, etc.) to make a corresponding adjustment to the position, as shown in FIG. 11b, thus realizing a more accurate operation such as liquid transfer, liquid intake or liquid refill, etc. Once the operation is completed, the user only has to release the thumb so that the dish lid can be closed. The Petri dish shown in FIGS. 11a and 11b is the Petri dish according to the embodiment shown in FIGS. 3-6; and the Petri dish shown in FIGS. 7-10 can be also operated similarly.

While the above detailed description of the application is made with reference to specific embodiments shown in the FIGS. 1 to 11b, those skilled in the art can make various modifications to the above specific embodiments. For example, the number of the spaced-apart ring sections for gripping and the gaps on the side wall of the dish body can be other than four, and they are preferably distributed evenly or symmetrically along the circumference of the side wall of the dish body so as to facilitating single-handedly opening the dish lid in different orientations. These ring sections for gripping and gaps are preferably the same in length and evenly distributed, serrations may also be formed on the outer circumference side of the ring sections for gripping to facilitate handheld operation. Further, the Petri dish can be also of other shapes than circular shape, for example, an oval shape. Even in some cases, the Petri dish can be of a polygon shape. When another shape other than circular shape is used for the Petri dish, the side wall lower portion of the side wall of the dish lid can be of a truncated cone shape which tapers from bottom to top, and the side wall upper portion of the side wall of the dish body can be of a truncated cone shape which tapers from top to bottom. The area of the space formed by the side wall upper portion of the dish lid can be slightly larger than the area of the lower end of the dish body, and the area of the upper end of the dish body can be slightly smaller than the area of the space formed by the side wall lower portion of the dish lid, thus facilitating taking and placing of the dish lid and enabling the Petri dishes to be stacked.

Fourth Embodiment

Figure 12:
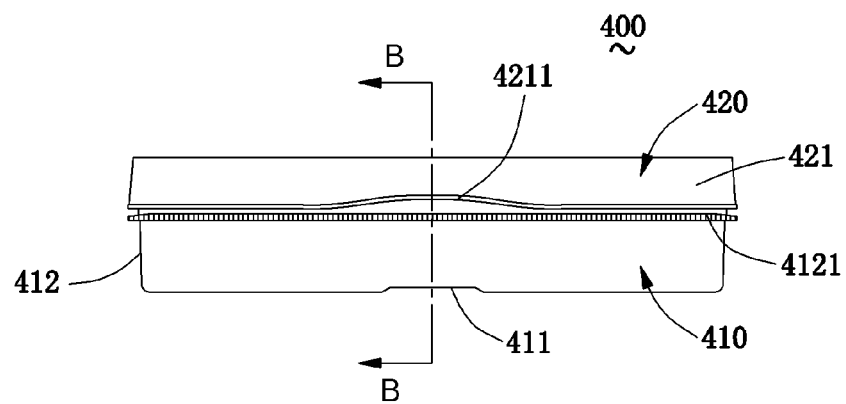
FIG. 12 is a schematic side view of a Petri dish according to a fourth embodiment of the present invention.

FIG. 12 is a schematic side view of a Petri dish according to the fourth embodiment of the present invention. In FIG. 12, reference sign 400 generally indicates a Petri dish, 410 indicates a dish body, 411 indicates a bottom wall of the dish body, 412 indicates a side wall of the dish body, 4121 indicates a ring for gripping on the side wall of the dish body, 420 indicates a dish lid, 421 indicates a side wall of the dish lid, and 4211 indicates an outwardly angled brim portion on the side wall of the dish lid.

Optionally, the Petri dish 400 can be a circular Petri dish. As can be seen in the figure, the Petri dish 400 comprises a dish body 410 and a dish lid 420, wherein the dish body 410 comprises a bottom wall 411 and a side wall 412, the dish lid 420 comprises a side wall 421 and a top wall 422 (see FIG. 13), and the dish lid 420 can be placed onto the dish body 410 to cover it. A ring for gripping 4121 is formed at the outside of the side wall 412 of the dish body 410, which enables the user to easily grip the dish body 410 without slide-off. The ring for gripping can either extend continuously along the entire circumference or be composed of several sections spaced-apart by gaps. Preferably but not necessarily, the outer periphery of the ring for gripping 4121 shown in FIG. 12 is serrated for facilitating a more stable grip. The ring for gripping 4121 is formed at such a position on the side wall 412 that it will not interfere with the side wall 421 of the dish lid 420, i.e., the opening and closing of the dish lid 420 will not be hampered. The outwardly angled brim portion 4211 is formed on the side wall 421 of the dish lid 420, i.e., the side wall 421 is partially angled up to form the angled up brim portion 4211. When it is intended to open the dish lid 420, it is only required to press the angled up brim portion 4211 towards the side wall 412 of the dish body 410 so that the dish lid 420 can pivot about a corresponding position of the side wall 412 of the dish body 410 and will be opened. It can be understood that the opening angle β of the dish lid 420 (see FIG. 14) will depend on the angled up angle of the outwardly angled brim portion 4211 relative to the side wall 412 of the dish body 410.

Figure 17A:
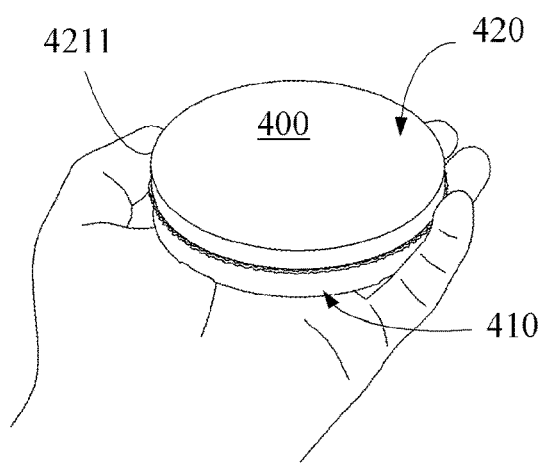
FIGS. 17a and 17b schematically show how the Petri dish according to the fourth embodiment of the present invention is operated.
Figure 17B:
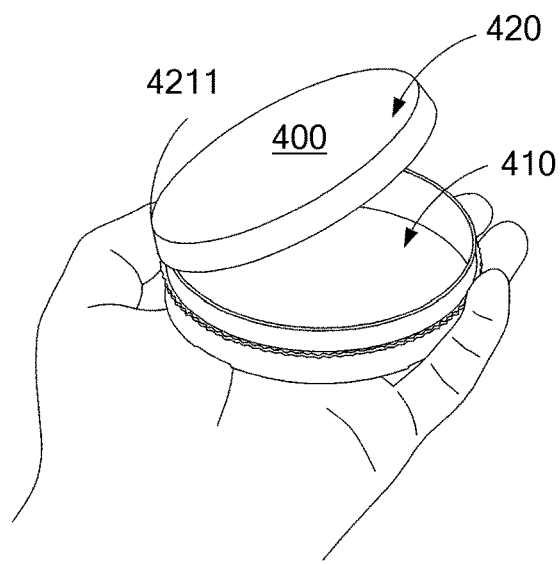

As shown in FIG. 12, this kind of Petri dish with an outwardly angled brim portion enables the user to open the dish lid while gripping the Petri dish single-handedly and conveniently. In such a design, the user can use the thumb to open the dish lid 420 by pressing the outwardly angled brim portion 4211, and when the thumb is released, the dish lid can be closed by the gravity of the dish lid itself. In the whole process of operation, the entire Petri dish 400 is held very stably by the palm and the other four fingers than the thumb, as shown in FIGS. 17*a* and 17*b*. Besides, such a design is also applicable to the single-handed operation of a small-sized Petri dish. It can be understood that in an alternative embodiment, the ring for gripping 4121 can be omitted.

Figure 13:
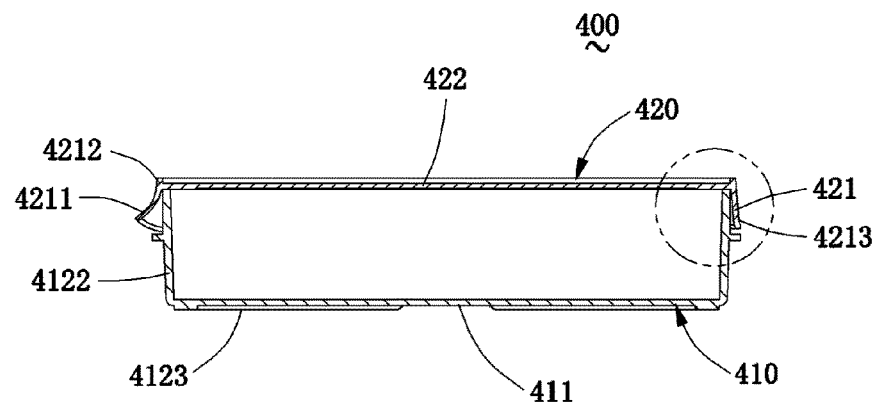
FIG. 13 is a schematic sectional view taken along the line B-B in FIG. 12, wherein the Petri dish is shown in a closed state.

FIG. 13 is a schematic sectional view taken along the line B-B in FIG. 12, wherein the Petri dish is shown in a closed state. In FIG. 13, the reference sign 422 indicates the top wall of the dish lid 420.

For the purpose of facilitating description, the portion of the side wall 421 of the dish lid 420 that is above the top wall 422 is referred to as side wall upper portion 4212, and the portion of the side wall 421 of the dish lid 420 that is below the top wall 422 is referred to as side wall lower portion 4213. As shown, the side wall upper portion 4212 and the side wall lower portion 4213 can respectively define an upper receiving space and a lower receiving space that are above and below the top wall 422 of the dish lid 420 respectively. Generally, the length by which the side wall upper portion 4212 extends in an axial direction of the dish lid is shorter than the length by which the side wall lower portion 4213 extends in an axial direction of the dish lid. That is, the upper receiving space is shallower than the lower receiving space. The diameter of the upper receiving space defined by the side wall upper portion 4212 is slightly larger than an outer diameter of an end portion at a lower end of the dish body 410. That is, the area of the upper receiving space formed by the upper portion of the side wall of the dish lid is slightly larger than the area of the lower end of the dish body. The diameter of the lower receiving space defined by the side wall lower portion 4213 is slightly larger than an outer diameter of an end portion at an upper end of the dish body 410. That is, the area of the lower receiving space formed by the lower portion of the side wall of the dish lid is slightly larger than the area of the upper end of the dish body. It can be understood that such a design enables two identical Petri dishes to be stacked on each other by simply placing one Petri dish into the upper receiving space at the top of the other Petri dish. Moreover, the dish cover 420 can easily cover the dish body 410. In a preferred but non-necessary embodiment, in order to facilitate the opening and closing of the dish lid 420 on the dish body 410, the side wall lower portion 4213 of the dish lid as well as the lower receiving space defined by the side wall lower portion 4213 can be designed to have a truncated cone shape, wherein the inner diameter at the lower end is slightly larger than the inner diameter at the position where it is joined to the top wall 422 of the dish lid 420. These features can be seen more clearly with reference to FIG. 15. However, for the present invention, these features are also optional, not indispensable. For example, in some specific embodiments, it is also possible that the dish lid is not provided with the above described receiving spaces.

For the purpose of facilitating description, the portion of the side wall 412 of the dish body 410 that is above the bottom wall 411 is referred to as side wall upper portion 4122, and the portion of the side wall 412 of the dish body 410 that is below the bottom wall 411 is referred to as side wall lower portion 4123. The side wall upper portion 4122 and the side wall lower portion 4123 respectively define an upper opening space and a lower opening space that are above and below the bottom wall 411 of the dish body 410 respectively. The upper opening space defined by the side wall upper portion 4122 is used for receiving cultures, and the lower opening space defined by the side wall lower portion 4123 is an air circulating space for avoiding a contact between the bottom wall 411 of the dish body 410 and other objects under the Petri dish, thus keeping the bottom wall 411 from an influence exerted by uneven temperatures. Meanwhile, such a design in structure can also increase the structural strength at the bottom of the dish body. In a preferred but non-necessary embodiment, the side wall lower portion 4123 of the bottom wall 411 of the dish body 410 can have one or more gaps that are distributed circumferentially so that an air circulation can be realized between the lower opening space and the outside, thus achieving a temperature equilibrium at the bottom wall 411 of the dish body 410. The side wall 412 of the dish body 410 can be also designed to have a truncated cone shape, wherein the outer diameter at the lower end is slightly smaller than the inner diameter of the upper receiving space defined by the side wall upper portion 4212 of the dish lid 420. As shown, optionally in this embodiment, the side wall upper portion 4122 of the dish body 410 as well as the upper opening space defined by the side wall upper portion 4122 can be designed to have a truncated cone shape, and the outer diameter at the side wall lower portion 4123 is slightly smaller than the inner diameter of the upper receiving space defined by the side wall upper portion 4212 of the dish lid 420. The design of the truncated cone shape of the side wall portions of the dish body 410 and the dish lid 420 can also facilitate the ejection operation after molding. It can be understood that for the present invention, the truncated cone shape of the lower opening space and the side walls of the dish body and the dish lid is also optional, not indispensable. For example, in some specific embodiments, it is also possible that the Petri dish is not provided with these features.

Figure 14:
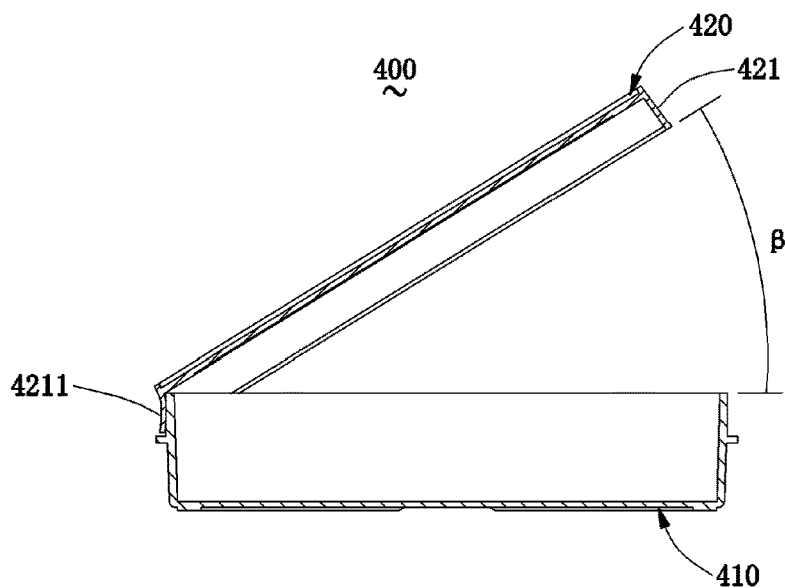
FIG. 14 is a schematic sectional view corresponding to FIG. 13, wherein the Petri dish is shown in an open state.

FIG. 14 is a schematic sectional view corresponding to FIG. 13, wherein the Petri dish is shown in an open state. The "β" in FIG. 14 is a maximum opening angle of the dish lid 420 relative to the dish body 410. The range of this angle is between 20 degrees and 70 degrees, and is preferably 45 degrees. As shown, such an angle is reached when the outwardly angled brim portion 4211 is pressed and abuts the side wall 412 of the dish body 410. A maximum opening angle β that is overly large or small may cause an unstable fit between the opened dish lid 420 and the dish body 410. The dish body and the dish lid in the present invention are two independent members that can be separated, or two members that are pivotally connected together so that they can pivot relative to each other. The former presents a flexible operation and the latter presents a highly stable operation.

Figure 15:
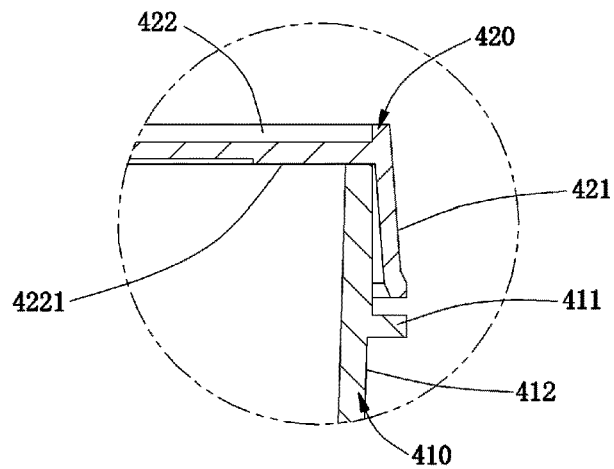
FIG. 15 is a partial enlarged schematic view of the circled portion in FIG. 13.

FIG. 15 is a partial enlarged schematic view of the circled portion in FIG. 13. As can be seen from FIG. 15, a plurality of spaced-apart protrusions 4221 are evenly distributed circumferentially at a position where the bottom face of the top wall 422 of the dish lid 420 is jointed to the inner side of the side wall 421. The protrusions 4221 enable a gap is formed between the bottom face of the top wall 422 of the dish lid 420 and the top portion of the side wall 412 of the dish body 410 so that air can pass through. As can be clearly seen from FIG. 15, the inner diameter at a position whether the side wall lower portion 4213 of the dish lid 420 is jointed to the top wall 422 is slightly larger than the outer diameter at the top end of the side wall upper portion 4122 of the dish body 410. The length by which the side wall lower portion 4213 of the dish lid 420 extends is smaller than the length by which the portion of the side wall upper portion 4122 of the dish body 410 that is above the ring for gripping 4121 extends so that the lower end of the side wall lower portion 4213 of the dish lid 420 and the outwardly angled brim portion 4211 will not interfere with the ring for gripping 4121.

Figure 16:
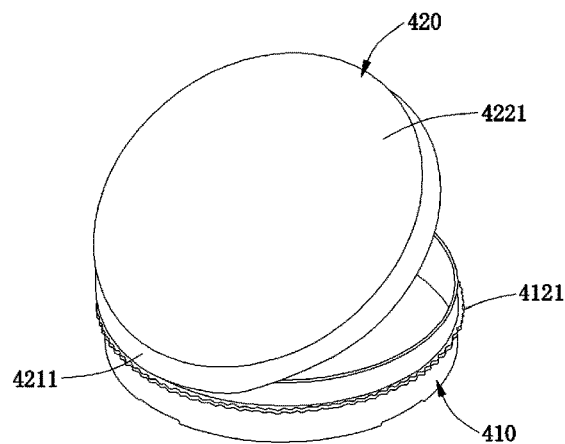
FIG. 16 is a perspective view of the Petri dish according to the above fourth embodiment of the present invention, wherein the Petri dish is shown in an open state.

FIG. 16 is a perspective view of the Petri dish according to the above fourth embodiment of the present invention, wherein the Petri dish is shown in an open state, which corresponds to the state shown in FIG. 14. As can be seen from FIG. 16, the outwardly angled brim portion 4211 on the side wall 422 of the dish lid 420 abuts the side wall 412 of the dish body 410. When a finger presses the outwardly angled brim portion 4211, the dish lid 420 and the dish body 410 can be held at a stable relative position. It should be understood that in order to make the outwardly angled brim portion 4211 and the side wall 412 of the dish body 410 completely abut along the circumference, such a design can be adopted in which the curvature of the outwardly angled brim portion 4211 is identical to the circular curvature of the side wall 412 of the dish body 410 so that the fit during contact is advantageous for holding the dish lid 420 and the dish body 410 at a more stable relative position. The length by which the outwardly angled brim portion 4211 extends along the circumference of the side wall of the dish lid should not be overly large or overly small. Otherwise, the dish lid will not fit with the dish body stably during opening. Ideally, the length by which the outwardly angled brim portion 4211 extends along the circumferential direction of the side wall of the dish lid corresponds to a central angle of 20 degrees to 80 degrees, and preferably corresponds to a central angle of 50 degrees.

FIGS. 17a and 17b schematically show how the Petri dish according to the fourth embodiment of the present invention is operated. When a user opens the Petri dish 400, the Petri dish can be hand-held as shown in FIG. 17a so that the whole Petri dish is in the palm and the position of the thumb aims at the outwardly angled brim portion 4211 of the dish lid. If the thumb does not aim at the outwardly angled brim portion properly, the thumb can turn the dish lid around so that the thumb can aim at the outwardly angled brim portion. When the user needs to open the Petri dish to perform an operation, he only has to press the outwardly angled brim portion 4211 with his thumb so that the dish lid 420 can be opened. At this time, the whole Petri dish is still steadily held in the palm, and the left hand can cooperate with the right hand (which grips an appliance such as the liquid transfer pipettor, etc.) to make a corresponding adjustment to the position, as shown in FIG. 17b, thus realizing a more accurate operation such as liquid transfer, liquid intake or liquid refill, etc. Once the operation is completed, the user only has to release the thumb so that the dish lid can be closed.

While the above detailed description of the application is made with reference to specific embodiments shown in the FIGS. 12 to 17b, those skilled in the art can make various modifications to the above specific embodiments. For example, the number of the outwardly angled brim portions on the side wall of the dish lid can be more than one, and preferably, the outwardly angled brim portions can be distributed evenly or symmetrically along the circumference of the side wall of the dish lid so that the dish lid can be opened at different orientations. In a simple embodiment, the ring for gripping on the side wall of the dish body can be omitted, or preferably, the ring for gripping can be composed of several spaced-apart sections. Of course, these sections are preferably of the same length and are distributed evenly, and serrations can be also provided on the outer circumference thereof for facilitating gripping. Further, the Petri dish can be also of other shapes than circular shape, for example, an oval shape. Even in some cases, the Petri dish can be of a polygon shape. However, this requires that the outwardly angled brim portion is angled up along the entire edge of the dish lid of the polygon shape so as to prevent the non-angled up portion from influencing the opening of the dish lid. When another shape other than circular shape is used for the Petri dish, the side wall lower portion of the side wall of the dish lid is of a truncated cone shape which tapers from bottom to top, and the side wall upper portion of the side wall of the dish body is of a truncated cone shape which tapers from top to bottom. The area of the space formed by the side wall upper portion of the dish lid is slightly larger than the area of the lower end of the dish body, and the area of the upper end of the dish body is slightly smaller than the area of the space formed by the side wall lower portion of the dish lid, thus facilitating taking and placing of the dish lid and enabling the Petri dishes to be stacked.

The specific embodiments of the present invention have been described in detail above with reference to the accompanying drawings. Those skilled in the art can make equivalent modifications or variations on the specific features in various embodiments according to the above description. It goes without saying that these modified embodiments will also fall within the scope of protection covered by the appended claims.

What is claimed is:

1. A Petri dish comprising:
a dish body having a bottom wall and a side wall which extends along an outer circumference of the bottom wall, the bottom wall and the side wall of the dish body forming an upper opening space adapted to accommodate cultures;
a dish lid adapted to cover the upper opening space from above the dish body, the dish lid having a top wall and a side wall which extends along an outer circumference of the top wall, the dish body and the dish lid being two independent members that are detachable;
a ring for gripping formed on an outer side of the side wall of the dish body that extends circumferentially, wherein the ring for gripping has an outer diameter larger than an outer diameter of the dish lid; and
a plurality of upwardly extending protrusions distributed on the ring for gripping,
wherein, when the dish lid is closed on the dish body, a lower end of the side wall of the dish lid is located between the side wall of the dish body and a first portion of the plurality of protrusions, and the lower end of the side wall of the dish lid is spaced in a vertical direction from the ring, with a second portion of the plurality of protrusions being located between the lower end of the side wall of the dish lid and the ring.

2. The Petri dish according to claim 1, wherein a top face of the protrusions is formed into an upwardly opening hook shape, and when the dish lid is closed on the dish body, the lower end of the side wall of the dish lid is located in a hook opening.

3. The Petri dish according to claim 1, wherein the plurality of protrusions are evenly distributed on the ring for gripping in a circumferential direction.

4. The Petri dish according to claim 1, wherein the Petri dish has a circular shape and an extension length between two of the plurality of protrusions along the circumferential direction of the side wall of the dish body corresponds to a central angle of 20 degrees to 80 degrees.

5. The Petri dish according to claim 1, wherein a maximum opening angle α of the dish lid relative to the dish body is between 20 degrees and 70 degrees.

6. The Petri dish according to claim 1, wherein a length by which a side wall lower portion of the dish lid extends in an axial direction of the dish lid is larger than a length by which a portion of a side wall upper portion of the dish body that is above the ring for gripping extends in an axial direction of the dish body.

7. The Petri dish according to claim 1, wherein the Petri dish has a non-circular shape.

8. The Petri dish according to claim 1, wherein the Petri dish has a circular shape and an extension length between two of the plurality of protrusions along the circumferential direction of the side wall of the dish body corresponds to a central angle of 50 degrees.

9. The Petri dish according to claim 1, wherein a maximum opening angle α of the dish lid relative to the dish body is 45 degrees.

10. The Petri dish according to claim 7, wherein the non-circular shape comprises one of rectangular, square, trapezoidal, triangular or oval.

11. A Petri dish comprising:
a dish body having a bottom wall and a side wall which extends along an outer circumference of the bottom wall, the bottom wall and the side wall of the dish body forming an upper opening space adapted to accommodate cultures;
a dish lid adapted to cover the upper opening space from above the dish body, the dish lid having a top wall and a side wall which extends along an outer circumference of the top wall, the dish body and the dish lid being two independent members that are detachable;
a ring for gripping formed on an outer side of the side wall of the dish body that extends circumferentially, wherein the ring for gripping has an outer diameter larger than an outer diameter of the dish lid; and
an upwardly angled brim portion provided on a radially outer circumference side of the ring for gripping, with the upwardly angled brim portion being angled in a direction extending radially away from the side wall of the dish body,
wherein, when the dish lid is closed on the dish body, the upwardly angled brim portion surrounds a lower end of the side wall of the dish lid.

12. The Petri dish according to claim 11, wherein the ring for gripping comprises ring sections for gripping spaced-apart by gaps, and the upwardly angled brim portion is located on the ring sections for gripping.

13. The Petri dish according to claim 12, wherein only an end portion of the ring sections for gripping is provided with the upwardly angled brim portion.

14. The Petri dish according to claim 12, wherein the ring sections for gripping are symmetrically or evenly distributed in a circumferential direction on the side wall of the dish body.

15. The Petri dish according to claim 12, wherein the Petri dish has a circular shape and a length by which the gaps extend in a circumferential direction of the side wall of the dish body corresponds to a central angle of 20 degrees to 80 degrees.

16. The Petri dish according to claim 11, wherein a maximum opening angle α of the dish lid relative to the dish body is between 20 degrees and 70 degrees.

17. The Petri dish according to claim 11, wherein a length by which a side wall lower portion of the dish lid extends in an axial direction of the dish lid is larger than a length by which a portion of a side wall upper portion of the dish body that is above the ring for gripping extends in an axial direction of the dish body.

18. The Petri dish according to claim 11, wherein the Petri dish has a non-circular shape.

19. The Petri dish according to claim 12, wherein the Petri dish has a circular shape and a length by which the gaps extend in a circumferential direction of the side wall of the dish body corresponds to a central angle of 50 degrees.

20. The Petri dish according to claim 18, wherein the non-circular shape comprises one of rectangular, square, trapezoidal, triangular or oval.

* * * * *

UNITED STATES PATENT AND TRADEMARK OFFICE
CERTIFICATE OF CORRECTION

PATENT NO. : 10,920,183 B2
APPLICATION NO. : 15/038908
DATED : February 16, 2021
INVENTOR(S) : Zheng et al.

It is certified that error appears in the above-identified patent and that said Letters Patent is hereby corrected as shown below:

In the Specification

In Column 4, Line 48, change "FIG. 10 is partial enlarged schematic view of the circled" to --FIG. 10 is a partial enlarged schematic view of the circled--.

In Column 6, Lines 19-20, change "the dish lid in which the users uses two ends of the gaps" to --the dish lid in which the user uses two ends of the gaps--.

In Column 8, Line 6, change "These protrusions enables a" to --These protrusions enable a--.

In Column 8, Line 33, change "The "a" in FIG. 5 is a maximum opening" to --The "α" in FIG. 5 is a maximum opening--.

In Column 9, Line 65, change "FIG. 10 is partial enlarged schematic view" to --FIG. 10 is a partial enlarged schematic view--.

In Column 10, Line 38, change "the dish body so as to facilitating single-handedly opening" to --the dish body so as to facilitate single-handedly opening--.

In Column 13, Line 14, change "angle (3 that is overly large or small" to --angle β that is overly large or small--.

In Column 13, Lines 32-33, change "the inner diameter at a position whether the side wall lower portion" to --the inner diameter at a position where the side wall lower portion--.

In the Claims

In Claim 12, Column 16, Lines 26-27, change "for gripping comprises ring sections for gripping spaced-apart by gaps," to --for gripping comprises ring sections for gripping spaced apart by gaps,--.

Signed and Sealed this
Fourth Day of May, 2021

Drew Hirshfeld
*Performing the Functions and Duties of the
Under Secretary of Commerce for Intellectual Property and
Director of the United States Patent and Trademark Office*